(12) United States Patent
Wienke et al.

(10) Patent No.: US 8,215,094 B2
(45) Date of Patent: Jul. 10, 2012

(54) CHAIN COMPRISING A PLURALITY OF INTERCONNECTED LINKS

(75) Inventors: Dietrich D. Wienke, Elsloo (NL); Christiaan Henri Peter Dirks, Dilsen (NL); Martinus Johannes Nicolaas Jacobs, Heerlen (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/361,867

(22) Filed: Jan. 30, 2012

(65) Prior Publication Data

US 2012/0124959 A1    May 24, 2012

Related U.S. Application Data

(63) Continuation of application No. 12/523,920, filed as application No. PCT/EP2007/009431 on Oct. 30, 2007, now Pat. No. 8,171,714.

(30) Foreign Application Priority Data

Jan. 22, 2007 (EP) .................................... 07001305

(51) Int. Cl.
   *F16G 1/22* (2006.01)
   *F16G 13/12* (2006.01)
(52) U.S. Cl. .......... 59/76; 59/84; 59/92; 59/93; 474/203

(58) Field of Classification Search .............. 59/78, 84, 59/90, 92, 93; 474/203
See application file for complete search history.

(56) References Cited

U.S. PATENT DOCUMENTS

| | | | |
|---|---|---|---|
| 4,250,764 | A | 2/1981 | Grant |
| 4,779,411 | A | 10/1988 | Kendall |
| 6,849,016 | B2 | 2/2005 | Ashtiani et al. |
| 7,294,078 | B2 | 11/2007 | He et al. |
| 2006/0259076 | A1 | 11/2006 | Burkhart et al. |

FOREIGN PATENT DOCUMENTS

| | | |
|---|---|---|
| EP | 1 063 449 | 12/2000 |
| WO | 2004/067434 | 8/2004 |
| WO | 2006/066970 | 6/2006 |

OTHER PUBLICATIONS

International Search Report for PCT/EP2007/009431, mailed Apr. 2, 2008.

*Primary Examiner* — David Jones
(74) *Attorney, Agent, or Firm* — Nixon & Vanderhye P.C.

(57) ABSTRACT

The invention relates to a chain suitable to moor or anchor boats, to lash cargo in road, rail, water and air transportation or for conveying, hoisting, suspending or lifting applications, said chain comprising a plurality of interconnected links. More in particular the invention relates to a chain suitable for the above stated uses comprising a plurality of interconnected links, at least part of the links comprising polyolefin fibers and in particular ultrahigh molecular weight polyethylene (UHMWPE) fibers. The invention also relates to a method for enhancing the strength of such a chain.

12 Claims, 4 Drawing Sheets

CHAIN COMPRISING A PLURALITY OF INTERCONNECTED LINKS

This application is a continuation of U.S. application Ser. No. 12/523,920 filed on 9 Nov. 2009 (now U.S. Pat. No. 8,171,714), which is the U.S. national phase of International Application No. PCT/EP2007/009431 filed 30 Oct. 2007, which designated the U.S. and claims priority to European Application No. 07001305.7 filed 22 Jan. 2007, the entire contents of each of which are hereby incorporated by reference.

The invention relates to a chain suitable to moor or anchor boats, to lash cargo in road, rail, water and air transportation or for conveying, hoisting, suspending or lifting applications, said chain comprising a plurality of interconnected links. More in particular the invention relates to a chain suitable for the above stated uses comprising a plurality of interconnected links, at least part of the links comprising polymeric fibres. The invention also relates to a method for enhancing the strength of such a chain.

A chain should desirably be capable of transmitting forces under all kinds of circumstances and environmental conditions, often for a prolonged period of time, without the chain being affected in any way, such as by breaking, fraying, damaging, and so on. Other requirements may also be important. During use in the above-mentioned operations, chains are subjected to substantial wear and tear conditions which may lead to extensive abrasion of the chain. Chains should therefore be durable. Chains for air transportation moreover should not only be strong and durable, but at the same time be as lightweight as possible, in order not to unduly increase the payload of an aircraft. A chain should also have a low risk for sudden failure. This is important in securing air cargo, where a sudden release of heavy weight cargo may be particularly disastrous.

A chain comprising a plurality of interconnected links, at least part of the links comprising polymeric multifilament yarns, is known from U.S. Pat. No. 4,779,411. The disclosed chain comprises links of aromatic polyamide (aramid) multifilament yarns, sheathed with a woven outer fabric. Although the chain known from U.S. Pat. No. 4,779,411 performs reasonably well, its service life is limited, in particular under dynamic loading conditions.

The object of the present invention is to provide a chain according to the preamble that is very well capable of transmitting forces and moreover shows improved durability over the prior art.

This object is achieved according to the invention by providing a chain comprising a plurality of interconnected links, wherein at least part of the links comprise polyolefin multifilament yarns.

In a chain, forces are transmitted from one link to another through the interconnections, where links make local mutual contact. At the contact points the links are highly stressed (mainly compressive), which easily leads to local damage or even fracture of the link. Surprisingly, when using polyolefin multifilament yarns, and ultrahigh molecular weight polyethylene multifilament yarns in particular, in the chain links, the service life of the chain is improved with respect to the prior art, in particular under dynamic loading conditions.

A suture is known from US Patent Application 2006/0259076 having a chain-like construction including at least two loops formed of Dyneema® (DSM) ultra high molecular weight long chain polyethylene (UHMWPE) multifilament yarns. However, the suture disclosed therein is too thin and too weak, i.e. very low static strength, to be used in heavy-duty applications like mooring or anchoring boats, lashing cargo in road, rail, water and air transportation or conveying, hoisting, suspending or lifting applications. Furthermore, the referred US application is silent with regard to heavy-duty applications as the present invention relates to. Yet furthermore, the requirements for a suture in terms of static strength are different than those for a chain designed for said heavy-duty applications. No disclosure is given in the referred US application regarding requirements for heavy-duty applications.

A chain according to the invention shows an unexpectedly high strength and durability and is damage tolerant. A chain according to the invention moreover shows an improved strength retention over the prior art. When a chain is used to transmit forces under variable circumstances, fatigue and friction induced local heat up may also become important. Although polyolefin multifilament yarns in general have limited temperature resistance, at least compared to metals for instance, these effects surprisingly do not occur in the chain according to the invention, at least not to such extent that performance is hampered.

Preferably, the static strength of the chain of the invention is at least 1 kN, more preferably at least 5 kN, even more preferably at least 10 kN, yet even more preferably at least 30 kN, yet even more preferably at least 50 kN, yet even more preferably at least 100 kN, yet even more preferably at least 1000 kN, yet even more preferably at least 10,000 kN, yet even more preferably at least 50,000 kN, yet even more preferably at least 100,000 kN, yet even more preferably at least 150,000 kN, yet even more preferably at least 500,000 kN, most preferably at least $10^6$ kN.

By static chain strength is herein understood the strength of the chain when the chain is subjected to a static load.

Polyolefin multifilament yarns are used in the chain according to the invention. These multifilament yarns are known per se, and have an elongated body whose length dimension exceeds the transverse dimensions of width and thickness. The elongated bodies may have a regular or irregular cross-section. Preferably, the polyolefin multifilament yarns used in the chain have a tensile strength of at least 1.2 GPa, more preferably at least 2 GPa, preferably at least 3 GPa, yet even more preferably at least 3.5 GPa, yet even more preferably at least 4 GPa, most preferably at least 5 GPa, and a tensile modulus of at least 40 GPa, more preferably at least 60 GPa, most preferably at least 80 GPa.

Homopolymers and copolymers of polyethylene and polypropylene are particularly suitable polyolefins for the production of the polyolefin multifilament yarns. The polyolefins may contain small amounts of one or more other polymers, in particular other alkene-1-polymers. A particularly preferred polyolefin comprises UHMWPE, having a weight average molecular weight of at least 400,000 g/mol. Preferably, the UHMWPE has less than 1 side chain per 300 C atoms, more preferably less than 1 side chain per 100 C atoms. The UHMWPE multifilament yarns applied in the chain according to the invention may further contain small amounts, generally less than 5% by weight, preferably less than 3% by weight, of customary additives, such as antioxidants, thermal stabilizers, colorants, flow promoters, and so on.

Preferably UHMWPE multifilament yarns are used which comprise UHMWPE filaments, prepared by a gel spinning process. A suitable gel spinning process is described in for example GB-A-2042414, GB-A-2051667, EP 0205960 A and WO 01/73173 A1, and in "Advanced Fibre Spinning Technology", Ed. T. Nakajima, Woodhead Publ. Ltd (1994), ISBN 185573 182 7. In short, the gel spinning process comprises preparing a solution of a UHMWPE of high intrinsic viscosity in a solvent, spinning the solution into filaments at a temperature above the dissolving temperature, cooling down the filaments below the gelling temperature, and drawing the filaments before, during and/or after at least partial removal of the solvent.

The preferred polyolefin multifilament yarn comprises a multifilament yarn of UHMWPE with an intrinsic viscosity preferably between 5 dl/g and 40 dl/g, determined in decalin at 135° C., and a yarn titre of at least 50 denier, with the yarn having a tensile strength of at least 2.5 N/tex, more preferably at least 3.0 N/tex, even more preferably at least 3.2 N/tex, even more preferably at least 3.4 N/tex. More preferably, the yarn titer is at least 100 denier, even more preferably at least 1000 denier, yet even more preferably at least 2000 denier, yet even more preferably at least 3000 denier, yet even more preferably at least 5000 denier, yet even more preferably at least 7000 denier, most preferably at least 10000 denier. Preferably, the polyolefin and more in particular the UHMWPE multifilament yarns forming a chain link have a total titre of at least $1 \times 10^n$ dtex, wherein n is an integer of preferably at least 3, more preferably at least 4, even more preferably at least 5, yet even more preferably at least 6, yet even more preferably at least 7, yet even more preferably at least 8, most preferably at least 9. If desired, the UHMWPE multifilament yarns may comprise a mixture of two or more polyethylenes, differing for instance in intrinsic viscosity, molecular weight distribution, and/or type and number of comonomers or side chains. The intrinsic viscosity is determined according to PTC-179 (Hercules Inc. Rev. Apr. 29, 1982), adopting a dissolution time of 16 hours, using an amount of 2 g/l solution of DBPC as anti-oxidant, measuring the viscosity at different concentrations, and extrapolating to zero concentration. Tensile strength (or tenacity) of the UHMWPE multifilament yarns is determined according to ASTM D885M.

A further advantage of the use of polyolefin multifilament yarns, and particularly UHMPWE multifilament yarns, in the links of a chain is that an unexpectedly high static chain strength is obtained. The durability under fatigue loading, and/or the strength in humid conditions are also improved over the prior art. Humid conditions refer to environments wherein the degree of humidity is on average higher than 50%, more preferably higher than 80% and most preferably higher than 99%. By fatigue loading is herein understood dynamic loading conditions.

The chain is further advantageously used in marine applications for instance, where the chain comes in direct contact with water.

The chain according to the invention has a low specific gravity, which makes it particularly suitable in applications where low weight is important. Further, its environmental resistance is good, particularly against acids. Other advantages include its softness, low noise and non-corrosive characteristics, ease of handling, and ease of deployment. The chain moreover does not substantially conduct electrical current and/or heat, is relatively non-magnetic, and has a relatively low dielectric constant. It also exhibits low radar and infrared signature, which may be advantageous for military applications for instance.

Another preferred embodiment of the chain according to the invention is characterised in that at least part of the links comprise glass fibers, carbon fibers, metal fibers, aromatic polyamide fibers, poly(p-phenylene-2,6-benzobisoxazole) (PBO) fibers, M5 fibers, and/or poly(tetrafluoroethylene) (PTFE) fibers. The term fibers includes but is not limited to a filament, a multifilament yarn, a tape, a strip, a thread, a staple fibre yarn, and other elongated bodies may have having a regular or irregular cross-section. According to another preferred embodiment, at least part of the links of the chain consists of said fibres. Such a chain may have different properties along the length of the chain. For instance, some parts of the chain may have mechanical properties favourable to withstanding dynamic loading conditions, while other parts may have mechanical properties favourable to withstanding static loading conditions. Another possibility is that parts of the chain may be made lighter than water (these parts will generally comprise polyolefin multifilament yarns) while other parts may be made heavier than water. It is also possible that some links comprise said fibers in combination with polyolefin multifilament yarns, for example in the form of hybrid yarns. More preferred, at least part of the links comprise at least 51 vol. % of UHMWPE multifilament yarns, even more preferred at least 75 vol. %, even more preferred at least 90 vol. %, and most preferred at least 95 vol. %. A particularly preferred chain is characterised in that all links consist of UHMWPE multifilament yarns.

A further advantage of the use of polyolefin multifilament yarns, and more in particular UHMWPE multifilament yarns, is that a more reliable chain is obtained than the known chains, based on metal or on other polymeric fibres, such as aromatic polyamide fibers, for instance.

The multifilament yarns or fibers may have any construction known in the art, and/or may be combined in any textile construction known in the art. It is possible for instance to make the links of the chain in the form of endless loops of fibre bundles or yarns, extending more or less parallel to each other. A particularly preferred chain has links that comprise at least partly fused polyolefin multifilament yarns. Links that comprise at least partly fused polyolefin multifilament yarns may be present in the chain in the form of rings, loops, roundslings, and so on, and preferably also comprise a cover for protection and/or load distribution. Links that comprise at least partly fused polyolefin multifilament yarns may be manufactured by winding a multifilament yarn of the polyolefin around a pair of wheels to form a loop, heating the multifilament yarn to a temperature below the melting point of the multifilament yarn at which temperature the filaments at least partly fuse, and stretching the loop by increasing the distance between the wheels, while simultaneously rotating the wheels. By increasing the inter-wheel distance, the filaments are drawn. Chains comprising such links are strong and moreover distribute the loads between links particularly well.

Particularly preferred chains are characterised in that the links comprise straps of polyolefin multifilament yarns. By strap is meant herein a flexible, elongated body having a thickness that is much smaller than its width. Such straps are readily made by weaving or knitting the multifilament yarns into any construction, known in the art, such as a plain and/or twill weave construction for instance. The straps preferably have an n-ply webbing construction, where n is preferably at least 4, more preferably 3 and most preferably 2. The straps can be constructed with different tightness factors to adjust their mechanical properties, and more in particular their elongation to break. Preferred tightness factors are such that the straps have an elongation at break of at most 6%, and more preferred at most 4%. The tightness factor is herein defined as the number of yarns extending parallel to the longitudinal direction of the strap multiplied by the titre of the yarn per unit length. The width of the straps may be varied over a large range, with preferred widths at least 1.0 cm, more preferred at least 2.0 cm, even more preferred at most 30 cm, and most preferred at most 25 cm. The thickness of the straps is preferably chosen such that their ratio of width to thickness is at least 5:1, more preferably at least 10:1, the ratio of width to thickness moreover preferably being at most 40:1, and even more preferably at most 20:1. By limiting the width to thickness ratio of the straps, the links of the chain are more easily accessible for attachment means, such as hooks for instance.

In another preferred embodiment of the invention the chain links comprise an endless rope or tape, generally called a rope or tape sling. The advantage of a roundsling is that connections to each other or to a fitting having an eye for instance can be made with simple known knots, hitches or bends, which also show relatively high knot strength retention. Such a knot is for example the cow hitch, also called bale sling hitch, ring hitch, or tag knot. Such a knot can be made by passing one loop end of the sling through an eye, or a mesh, and then passing this loop through the opening formed by the other end of the sling (also called tail), and subsequently pulling the first end to tighten the knot. The person skilled in the art may easily select other suitable knots, for example the so-called double ring hitch, the Kellig hitch, or Prusik and Klemheist knots. These and other knots, and methods to make them can be found in the 'Handbook of knots', (Dorling Kindersley Book, London 1998; ISBN 0751305367), and in "The Ashley book of knots' (Faber and Faber Ltd, London 1990; ISBN 057109659x).

A rope or tape sling can be made by known methods, for example by connecting a certain length of rope or webbing end-to-end by sewing, knotting, splicing or welding. For ropes, preferably, the thickness of the end-to-end connection is less than twice the thickness of the rope, because this improves the flexibility and ease of connecting to a fitting. In one embodiment, the sling is made by sewing both ends of a woven strap together. In another embodiment the ends of a braided or laid rope are connected with a splice. A sling is within the present application understood to include a double loop, or double eye, or a triple eye. Such constructions are known to the skilled person, and can for example be made by splicing a loop on each end of a rope, or by making one or more connections, e.g. by sewing, preferably in the middle part of a sling. Preferably, the sling is coated and/or covered with tape or with a fabric to protect the fibres and/or to increase further its abrasion resistance. The sling may also comprise a core formed by a plurality of windings of multifilament yarns, preferably essentially parallel multifilament yarns, and a covering sheath, e.g. a woven or braided tubular fabric, and/or a sheath made from polyester, (aromatic) polyamide, or polyolefin multifilament yarns, or from a mixture thereof. Another advantage of the chain according to the invention is that a covering sheath is not necessary to obtain the desired performance.

Preferably, at least part of the links of the chain comprises multifilament yarns that have been combined with a suitable resin. Any resin able to form a suitable composite with the multifilament yarns may be used, although silicone resins and bitumen are the preferred resins. A chain according to this embodiment has links which deform to a lesser extent when the chain is stretched. This is advantageous when objects, such as hooks for instance, have to be attached to the chain especially when the chain is under load. The resin also offers further protection against damage development during dynamic loading conditions for instance.

The chain structure may be any structure known in the art. A preferred embodiment of the chain according to the invention is characterised in that the links of the chain comprise interconnected endless loops. Such chains are easily tailored according to their needs. For instance, their length is easily adjusted by adding or removing loops. Adding loops is for instance carried out by running several windings of the fiber through an existing loop, and subsequently securing the newly made loop preferably by stitching. Also side chains may easily be added to the (main) chain in a similar manner. This embodiment of the chain according to the invention also has an improved strength, since the loops are endless, and therefore do not have many cut ends.

The endless loops may also be interconnected by all means known in the art. The many options available to interconnect the loops is at least partly due to the use of UHMWPE multifilament yarns in the chain, particularly since these multifilament yarns show an improved load distribution capability over other polymeric multifilament yarns. Preferably the interconnected endless loops are interconnected by knots. This does not substantially affect chain performance, and is a very expedient way of interconnecting the loops. Another preferred embodiment is characterised in that the interconnected endless loops are interconnected by tubular connecting means. Such means offer improved load distribution, and are preferably filled with another material, such as a resin.

Another preferred chain structure according to the invention comprises a ladder. Such a ladder structure is easily made, out of rope for instance, and provides improved strength. Moreover, the links in such a ladder structure are deformable, yet provide easy access for other parts such as fixation means in the form of hooks for instance.

In still another embodiment the chain according to the invention is characterised in that the links are interconnected by connecting means which are preferably ring shaped. In such an embodiment the links preferably comprise straps of UHMWPE multifilament yarns. They may be attached to the connecting means by any suitable means, but preferably by stitching. In a preferred embodiment, the ring shaped connecting means may have different shapes as for example a circle, an oval, a triangular or a rectangular shape and may be made of any suitable material, including metal.

The components of the chain, such as the links and the connecting means, may be fixed to each other and/or to another structure by applying any suitable fixation means. Suitable fixation means include stitches, splicing and adhesives for instance. Preferably, the fixation means are stitches, because they can be easily applied in a well-controlled manner, at the desired location. Preferably, stitching is done with a yarn containing high-strength fibers.

In a further embodiment the fixation means are adhesives, preferably liquid adhesives that can be cured after application. The liquid adhesive is preferably injected into the connection means, such as an applied knot, and then cured to fixate the connection means. Connections can also be made by locally applying heat whereby the multifilament yarns at least partly melt and fuse together.

The chain according to the invention may also comprise means to attach it to another structure such as a pallet for instance. In this case, pallet attachment fittings, such as double studs, may be connected to the chain. Fittings, and hooks, are generally made from metal, although engineering plastics could alternatively be used. In a preferred embodiment, fittings and hooks are made of light weight metal, preferably magnesium. Such light-weight yet strong fittings further contribute to weight reduction of the chain.

The invention also relates to a method to enhance the mechanical properties, in particular the strength of a chain according to the invention.

It was found that the mechanical properties of the chain according to the invention, in particular its strength can be improved by pre-stretching the chain prior to its use below the melting point of the polyolefin, more preferably between 80-120° C., and most preferably between 90-110° C.

In a preferred embodiment of the method, the chain according to the invention is pre-stretched at a temperature below the melting temperature $T_m$ of the polyolefin, by applying a static load of at least 20%, more preferably at least 40%, and most preferably at least 60% of the breaking load of the chain for a period of time long enough to achieve a permanent deformation of the chain of between 2 and 20%, and more preferably between 5 en 10%. By permanent deformation is herein understood the extent of the deformation from which the chain cannot anymore recover.

In a second preferred embodiment of the method, the chain according to the invention is subjected to a number of load cycles. Preferably, the number of cycles ranges from 2-25, more preferably from 5-15, and most preferably from 8-12, whereby the maximum load applied is lower than 45% of the breaking load of the chain, more preferably lower than 35% of the breaking load of the chain, and most preferably lower than 25% of the breaking load of the chain. It is possible according to the invention to unload the chain during load cycling. In a preferred method however, the minimum load applied is at least 1%.

In a fourth preferred embodiment, the chain is prestretched as explained hereinabove at room temperature.

The invention will now be further explained by the following figures, without however being limited thereto. Herein.

Figure 1:
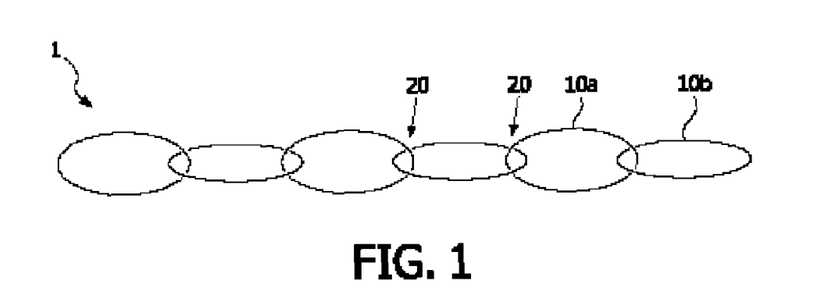
FIG. 1 schematically represents a first embodiment of a chain according to the invention.

Referring to FIG. 1 a chain 1 is shown comprising a plurality of interconnected links 10. The links 10 comprise interconnected endless loops, made by successively inserting a second open loop into a first already closed loop, and closing the second loop, for instance by using known techniques utilized in the textile industry, such as stitching, and/or by adhesive bonding. The loops 10 are roundslings, but any fibrous structure may be used. The connections 20 between the links 10 are formed by parts of the loop surfaces, which upon stretching of chain 1 impinge upon each other. This way of load transfers between links 10 results in locally high (compressive) stresses. The use of ultrahigh molecular weight polyethylene multifilament yarns in the links provides improved resistance against these stresses. Another advantage is that chain 1 can be easily adjusted in length by attaching more links to an already existing part, or by removing links. It is also very easy to add side-links to the chain. Links 10 may have any form, may differ from each other, and may extend in different planes, as shown in FIG. 1 where links 10a are in the plane of the figure, and links 10b perpendicular thereto.

Figure 2:
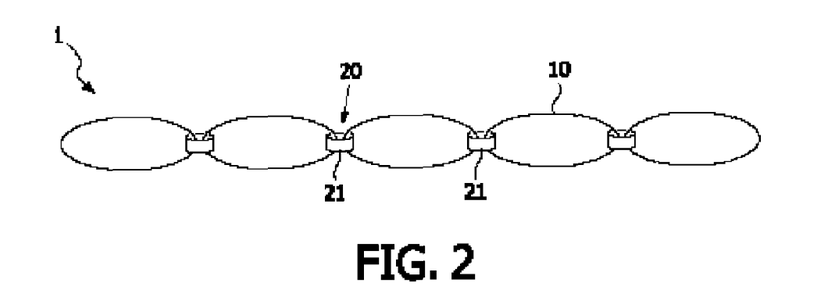
FIG. 2 schematically represents an improvement of the embodiment shown in FIG. 1.

FIG. 2 shows an improvement over the chain of FIG. 1. This embodiment has interconnected endless loops 10 that are interconnected by tubular connecting means 21. Connecting means 21 preferably have an inner surface shaped such that load transfer between loops 10 is well distributed. Connecting means 21 may be filled with resin to obtain a more rigid connection between the loops 10. A further advantage of this embodiment is that the loops 10 are more easily accessible for hooks and/or other loops and the like, since the connecting means 21 act to keep the loops 10 open, at least in their vicinity.

Figure 3:
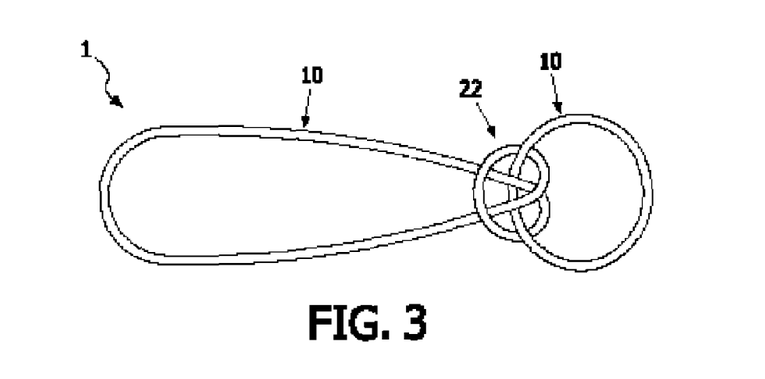
FIG. 3 schematically represents two loops of another improvement of the embodiment of FIG. 1.

Another preferred variant of the chain is shown in FIG. 3. Here, the interconnected endless loops 10 are interconnected by knots 22, in particular a cow-hitch knot. Although only two loops 10 are shown in FIG. 3, a chain obviously will have many more loops 10 in general.

Figure 4:
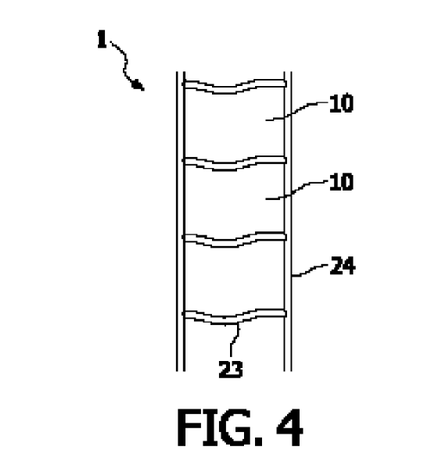
FIG. 4 schematically represents another embodiment of a chain according to the invention.
Figure 5:
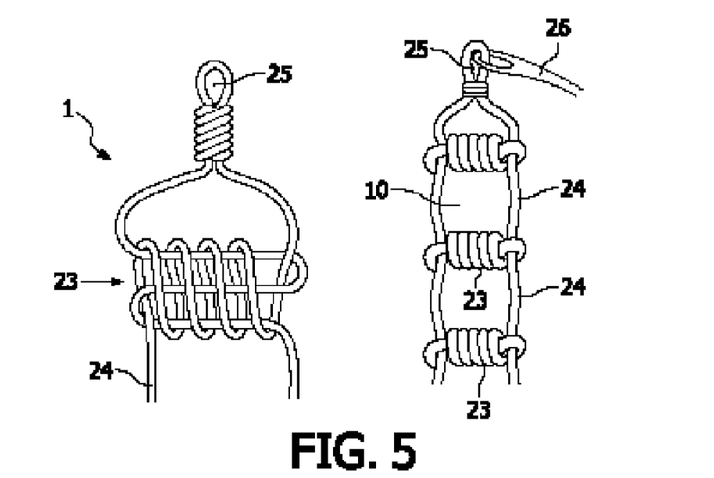
FIG. 5 schematically represents a detail of the embodiment shown in FIG. 4.

Still another preferred embodiment of the chain according to the invention is shown in FIGS. 4 and 5. Referring to FIG. 4, the chain 1 comprises a ladder structure, consisting of stiles 22 and steps 23. Stiles 22 and steps 23 together define a plurality of loops 10. Steps 23 form the connection between the loops 10. The ladder 1 may be made of any suitable fibrous structure, such as a rope, a webbing, a sling, a yarn, and so on. FIG. 5 shows a detail of how stiles 22 and steps 23 can be continuously formed of ultrahigh molecular weight polyethylene rope. The left figure shows an expanded view of the structure in this particular embodiment. Not only can a ladder chain 1 be made out of essentially one rope, which offers improved load transfer at the connections, but this particular embodiment also allows to readily incorporate additional attachment structures, such as eyes 25 for hooks or other attachment means 26.

Figure 6:
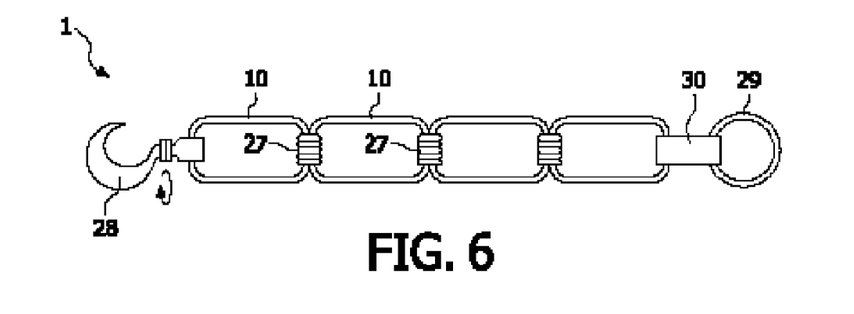
FIGS. 6, 7 and 8 schematically represent three other embodiments of a chain according to the invention.

Referring to FIG. 6, still another embodiment of the chain 1 according to the invention is shown. The chain 1 has a plurality of loops 10 in the form of ultrahigh molecular weight polyethylene fibrous structures, such as yarns and/or slings, interconnected by wraps 27 of another fibrous structure, preferably also out of ultrahigh molecular weight polyethylene. The chain further has a hook 28 attached to it, and a ring 29. The connection of ring 29 to the rest of the chain is formed by a strap 30, preferably also out of ultrahigh molecular weight polyethylene. This embodiment shows that a chain can easily be build up from several components, thereby providing great flexibility in use. Several components, such as hook 28, and ring 29 may be made from another material, such as metal, if desired.

Figure 7A:
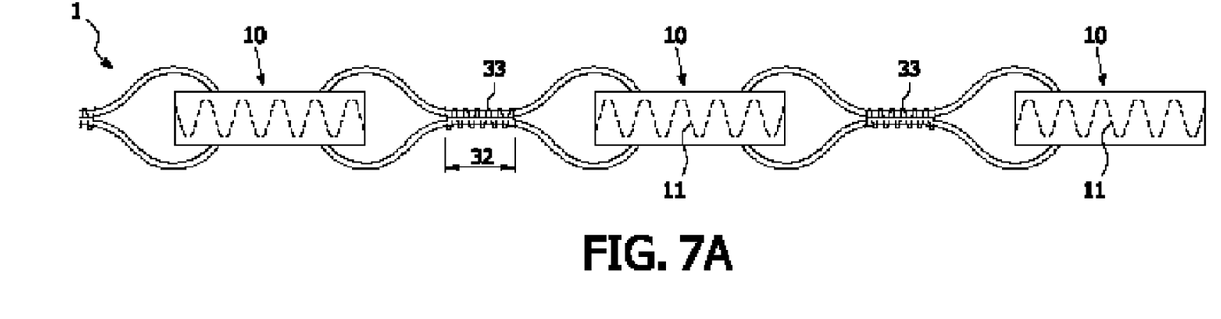
Figure 7B:
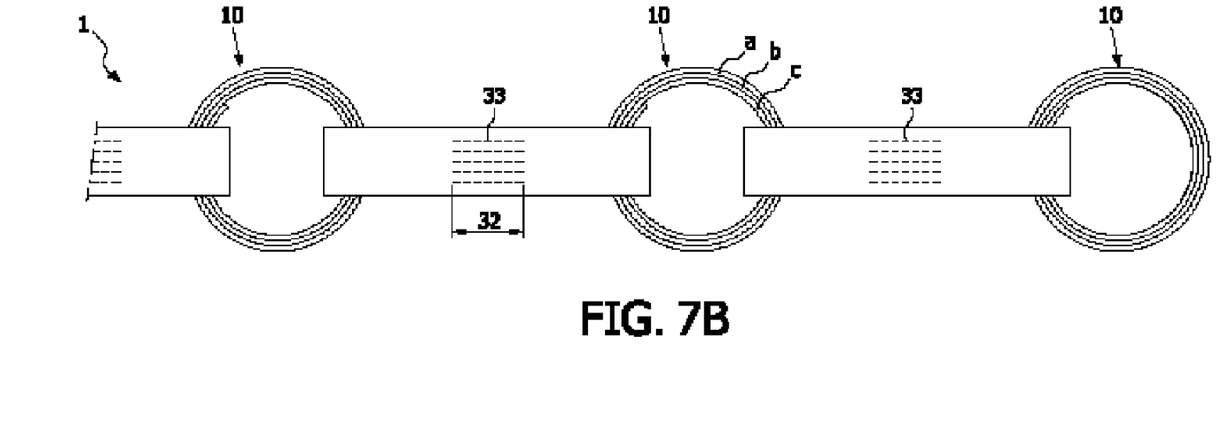

In FIGS. 7A and 7B another preferred embodiment of the chain 1 is shown. FIG. 7A is a side view, while FIG. 7B represents a top view. Chain 1 is build up of loops 10 in the form of rings. Rings 10 are formed by winding several layers of a fibrous structure of ultrahigh molecular weight polyethylene. Three layers (a to c) are shown, but there may be more or less, depending on the desired loads bearing capacity. The layers of rings 10 are held together by bonding them, for instance by stitchings 11. Rings 10 are interconnected by looped straps 31, opposite sides of which are bonded over at least a central portion 32. Binding can be done by stitches 33, but other means of bonding may also be used. If desired, stitches 33 may be omitted, for instance when a more flexible chain is needed.

Figure 8:
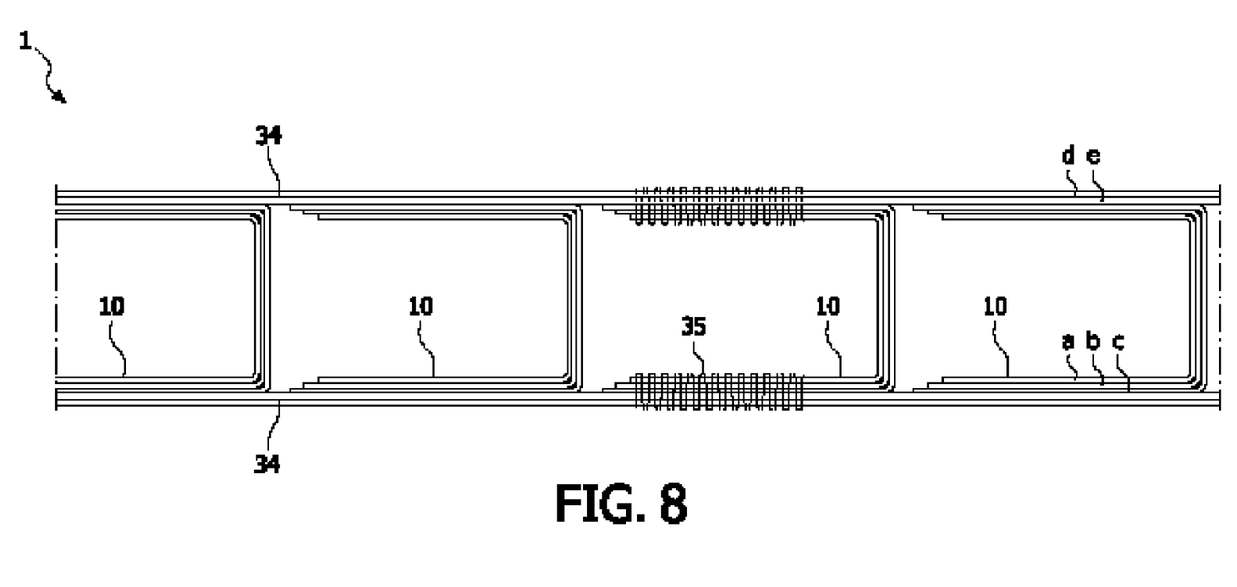

Finally FIG. 8 shows still another embodiment of the chain 1 according to the invention. This chain 1 is build up of U-shaped fibrous structures 10, which form the links of the chain. Each structure consists of several layers of a fibrous structure of ultrahigh molecular weight polyethylene. Three layers (a to c) are shown, but there may be more or less, depending on the desired loads bearing capacity. The U-shaped links 10 are assembled and attached to two stiles 34, also build of several layers of a fibrous structure of ultrahigh molecular weight polyethylene, in the variant shown two layers (d, e). Links 10 and stiles 34 are bonded to each other, for instance by stitching. In FIG. 8 stitches 35 are shown for one link only.

The present invention will now be further elucidated by the following examples and comparative experiments. Tests comparing the invention with the prior art, according to U.S. Pat. No. 4,779,411 (chain based on aramid) were conducted. A first series of tests included tensile testing of yarns and tensile testing of chains, made of these yarns. A second series of tests included abrasion tests, carried out on chains under dry and wet conditions.

Tensile testing was performed on dry samples using a Zwick 1484 Universal test machine at a temperature of approximately 21° C., and at a speed of 100 mm/min. Yarn samples were tested using standard fiber grips; chain samples were tested using D-shackles.

Abrasion testing was performed on a spoke wheel abrasion tester Static Abrasion Test, used in the rope and cable industry. The sample is in contact with a rotating body (spoke wheel, diameter 0.15 m) that contains 20 rods of 15 mm diameter parallel to the rotation axis of the body. The sample is loaded, usually with a certain fraction of the breaking load. The test can be done dry or wet, in the latter situation there is a continuous feed of water to the part of the sample in contact with the spoke wheel. The speed of the wheel was 2 rotations/sec, the load on the chain sample was 6% of the breaking strength. The number of cycles until failure was recorded.

EXAMPLE I

The breaking load and tenacity of Dyneema® SK75 yarn of 1760 dtex (=1760 g for 10000 m), obtained from DSM Dyneema B.V., the Netherlands, were determined. Tensile testing was performed as mentioned above. Results are summarized in Table 1.

EXAMPLE II

The breaking load and tenacity of a chain, made of Dyneema® SK75 yarn of DSM Dyneema B.V., the Netherlands, were determined. The chain had 4 engaging loops of 16 Dyneema® SK75 yarns of 1760 dtex. The sample chains were fixed by air-splicing. Tensile testing was performed as mentioned above. Results are summarized in Table 1.

Comparative Experiment A

The breaking load and tenacity of Twaron® 2000 yarn of 1580 dtex (=1580 g for 10000 m), obtained from Tejin Twaron, B.V., the Netherlands, were determined. Tensile testing was performed as mentioned above. Results are summarized in Table 1.

Comparative Experiment B

The breaking load and tenacity of a chain, made of Twaron® 2000 yarn of Tejin Twaron, B.V., the Netherlands, were determined. The chain had 4 engaging loops of 20 Twaron® 2000 yarns of 1580 dtex. The sample chains were fixed by air-splicing. Tensile testing was performed as mentioned above. Results are summarized in Table 1.

TABLE 1

Results of tensile tests on yarns and chains

| Sample | Weight (dtex) | Breaking load (N) | Tenacity (cN/dtex) | Strain (%) |
|---|---|---|---|---|
| Example I | 1760 | 606 | 34.3 | 3.6 |
| Comparative Exp. A | 1580 | 309 | 19.6 | 2.7 |
| Example II | 56400 | 2835 | 5.03 | 3.2 |
| Comparative Exp. B | 63200 | 2364 | 3.8 | 2.6 |

EXAMPLE III

The number of cycles until failure was determined of a dry chain, made of Dyneema® SK75 yarn of DSM Dyneema B.V., the Netherlands. Three chains were tested. The chain had 4 engaging loops of 16 Dyneema® SK75 yarns of 1760 dtex. The sample chains were fixed by air-splicing. Abrasion testing was performed as mentioned above. Results are summarized in Table 2.

EXAMPLE IV

The number of cycles until failure was determined of a wet chain, made of Dyneema® SK75 yarn of DSM Dyneema B.V., the Netherlands. Three chains were tested. The chain had 4 engaging loops of 16 Dyneema® SK75 yarns of 1760 dtex. The sample chains were fixed by air-splicing. Abrasion testing was performed as mentioned above. Results are summarized in Table 2.

Comparative Experiment C

The number of cycles until failure was determined of a dry chain, made of Twaron® 2000 yarn of 1580 dtex (=1580 g for 10000 m), obtained from Tejin Twaron, B.V., the Netherlands. Three chains were tested. The chain had 4 engaging loops of 20 Twaron® 2000 yarns of 1580 dtex. The sample chains were fixed by air-splicing. Abrasion testing was performed as mentioned above. Results are summarized in Table 2.

Comparative Experiment D

The number of cycles until failure was determined of a wet chain, made of Twaron® 2000 yarn of 1580 dtex (=1580 g for 10000 m), obtained from Tejin Twaron, B.V., the Netherlands. Three chains were tested. The chain had 4 engaging loops of 20 Twaron® 2000 yarns of 1580 dtex. The sample chains were fixed by air-splicing. Abrasion testing was performed as mentioned above. Results are summarized in Table 2.

TABLE 2

Results of abrasion tests on chains

| Sample | #1 | #2 | #3 | Average |
|---|---|---|---|---|
| Example III | 642 | 631 | 651 | 641 |
| Comparative Exp. C | 70 | 74 | 91 | 78 |
| Example IV | 2228 | 2091 | 2726 | 2348 |
| Comparative Exp. D | 105 | 127 | 104 | 112 |

EXAMPLES V TO VIII

Finally, a chain was made using a strap, made of Dyneema® SK75 1760 dtex yarn of DSM High Performance Fibers B.V. The strap had a linear weight of 238000 dtex (Example V). From the straps several chains were produced having the structure of FIG. 7. The chains are composed of rings, the rings being formed of 4 wraps of the above mentioned strap and stitched together. In the chain of Example VI, the rings as produced had a circular shape. The chain of Example VII had rings as produced with a rectangular shape. Also a pretension was applied to the rings before they were stitched together. Finally, the chain of Example VIII was equal to that of example VII, but the chain was heat set at a temperature of 100° C. applying a permanent strain of 5%. Tensile testing was performed as mentioned above. Results are summarized in Table 3.

TABLE 3

Results of tensile tests on chains

| Sample | Weight (dtex * 1000) | Breaking load (N * 1000) | Tenacity (cN/dtex) |
|---|---|---|---|
| Example V | 238 | 42 | 17.6 |
| Example VI | 1900 | 105 | 5.5 |
| Example VII | 1900 | 115 | 6.1 |
| Example VIII | 1800 | 130 | 7.2 |

From the tensile test results mentioned above it can be concluded that on the basis of equal weight, a chain based on ultrahigh molecular weight polyethylene fiber is at least about 33% stronger than a chain based on aromatic polyamide fibers, according to U.S. Pat. No. 4,779,411. Indeed from Table 1 one learns that the tenacity of a chain based on ultrahigh molecular weight polyethylene fiber (Example II) is 5.0 cN/dtex, while the tenacity of a chain based on aromatic polyamide fibers (Comp. Exp. B) is only 3.8 cN/dtex.

From the abrasion test results mentioned above it can be concluded that a chain based on ultrahigh molecular weight polyethylene fiber shows a much improved service life during dynamic loading conditions than a chain based on aromatic polyamide fibers, according to U.S. Pat. No. 4,779,411. Indeed from Table 2 one learns that the number of cycles until failure of a chain based on ultrahigh molecular weight polyethylene fiber (Example III) is 641, while the number of cycles until failure of a chain based on aromatic polyamide fibers (Comp. Exp. C) is only 78 (about a factor of 8 shorter). For a wet condition the number of cycles until failure of a chain based on ultrahigh molecular weight polyethylene fiber (Example IV) is 2348, while the number of cycles until failure of a chain based on aromatic polyamide fibers (Comp. Exp. D) is only 112 (about a factor of 20 shorter).

The invention claimed is:

1. A chain suitable to moor or anchor boats, to lash cargo in road, rail, water and air transportation and for conveying, hoisting, suspending and lifting applications, said chain comprising a plurality of interconnected links, wherein at least part of the links comprise polyolefin fibers having a tenacity of at least 1.9 N/tex.

2. The chain according to claim 1, wherein it has a static strength of at least 1 kN.

3. The chain according to claim 1, wherein the polyolefin is ultrahigh molecular weight polyethylene.

4. The chain according to claim 1, wherein at least part of the chain links comprise a cover.

5. The chain according to claim 1, wherein at least part of the links comprise glass fibers, carbon fibers, metal fibers, aromatic polyamide fibers, poly(p-phenylene-2,6-benzobisoxazole) (PBO) fibers, M5 fibers, and/or poly(tetrafluoroethylene) (PTFE) fibers.

6. The chain according to claim 1, wherein the links comprise at least partly fused polyolefin filaments and/or staple fibers.

7. The chain according to claim 1, wherein the links comprise straps of polyolefin fibers.

8. The chain according to claim 1, wherein the interconnected links of the chain comprise interconnected endless loops.

9. The chain according to claim 1, wherein the interconnected endless loops are interconnected by knots.

10. The chain according to claim 1, wherein the interconnected endless loops are interconnected by tubular connecting means.

11. The chain according to claim 1, wherein the chain comprises a ladder structure.

12. The chain according to claim 1, wherein the links are interconnected by ring shaped connecting means.

* * * * *